US010292680B2

(12) United States Patent
Kim et al.

(10) Patent No.: US 10,292,680 B2
(45) Date of Patent: May 21, 2019

(54) ULTRASONIC PROBE AND MANUFACTURING METHOD THEREOF

(71) Applicants: SAMSUNG ELECTRONICS CO., LTD., Suwon-si (KR); Kyungpook National University Industry-Academic Cooperation Foundation, Daegu (KR)

(72) Inventors: Youngil Kim, Suwon-si (KR); Jong Keun Song, Yongin-si (KR); Baehyung Kim, Yongin-si (KR); Yongrae Roh, Daegu (KR); Eunsung Lee, Hwaseong-si (KR); Kyungil Cho, Seoul (KR); Minseog Choi, Seoul (KR)

(73) Assignees: SAMSUNG ELECTRONICS CO., LTD., Suwon-si (KR); KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 194 days.

(21) Appl. No.: 14/694,489

(22) Filed: Apr. 23, 2015

(65) Prior Publication Data

US 2015/0305713 A1    Oct. 29, 2015

(30) Foreign Application Priority Data

Apr. 23, 2014 (KR) .......................... 10-2014-0048771

(51) Int. Cl.
*A61B 8/00* (2006.01)
*B06B 1/02* (2006.01)
(Continued)

(52) U.S. Cl.
CPC .......... *A61B 8/4444* (2013.01); *B06B 1/0215* (2013.01); *B06B 1/0292* (2013.01);
(Continued)

(58) Field of Classification Search
CPC ............................ A61B 8/4444; A61B 8/4483
See application file for complete search history.

(56) References Cited

U.S. PATENT DOCUMENTS 6,589,180 B2 * 7/2003 Erikson ................ A61B 8/4483
257/E27.006
8,398,551 B2 * 3/2013 Adachi ................ A61B 8/4483
600/407
(Continued)

FOREIGN PATENT DOCUMENTS

EP           2 130 004      12/2009
KR    10-2013-0032653 A     4/2013
(Continued)

*Primary Examiner* — Luther Behringer
(74) *Attorney, Agent, or Firm* — Sughrue Mion, PLLC

(57) ABSTRACT

An ultrasonic probe includes a capacitive micromachined ultrasonic transducer (cMUT) array configured to generate ultrasonic waves, an integrated circuit to which the cMUT array is bonded, and a flexible printed circuit board having one end connected to the integrated circuit to output signals to the integrated circuit, the integrated circuit including pads provided on the integrated circuit and an anisotropic conductive film (ACF) provided on the pads, and the one end of the flexible printed circuit board being connected to the ACF to thereby connect the flexible printed circuit board to the integrated circuit.

7 Claims, 10 Drawing Sheets

(51) Int. Cl.
  *B06B 1/06* (2006.01)
  *B06B 1/08* (2006.01)
  *G01S 15/89* (2006.01)

(52) U.S. Cl.
  CPC ............ *B06B 1/0629* (2013.01); *B06B 1/085* (2013.01); *A61B 8/4405* (2013.01); *A61B 8/4483* (2013.01); *B06B 2201/20* (2013.01); *G01S 15/8915* (2013.01)

(56) References Cited

U.S. PATENT DOCUMENTS

| | | | |
|---|---|---|---|
| 2009/0122651 A1 | 5/2009 | Kupnik et al. | |
| 2010/0036257 A1* | 2/2010 | Sano .................... | A61B 8/4281 600/459 |
| 2010/0125209 A1* | 5/2010 | Lee ...................... | B06B 1/0629 600/459 |
| 2010/0204583 A1 | 8/2010 | Rhim et al. | |
| 2011/0059660 A1* | 3/2011 | Konkle .................. | A61B 8/00 439/781 |
| 2013/0253326 A1* | 9/2013 | Oaks .................... | A61B 8/4494 600/459 |
| 2013/0303920 A1* | 11/2013 | Corl ........................ | A61B 8/12 600/468 |

FOREIGN PATENT DOCUMENTS

| | | |
|---|---|---|
| KR | 10-2013-0107457 A | 10/2013 |
| WO | 2008/053193 A1 | 5/2008 |

\* cited by examiner

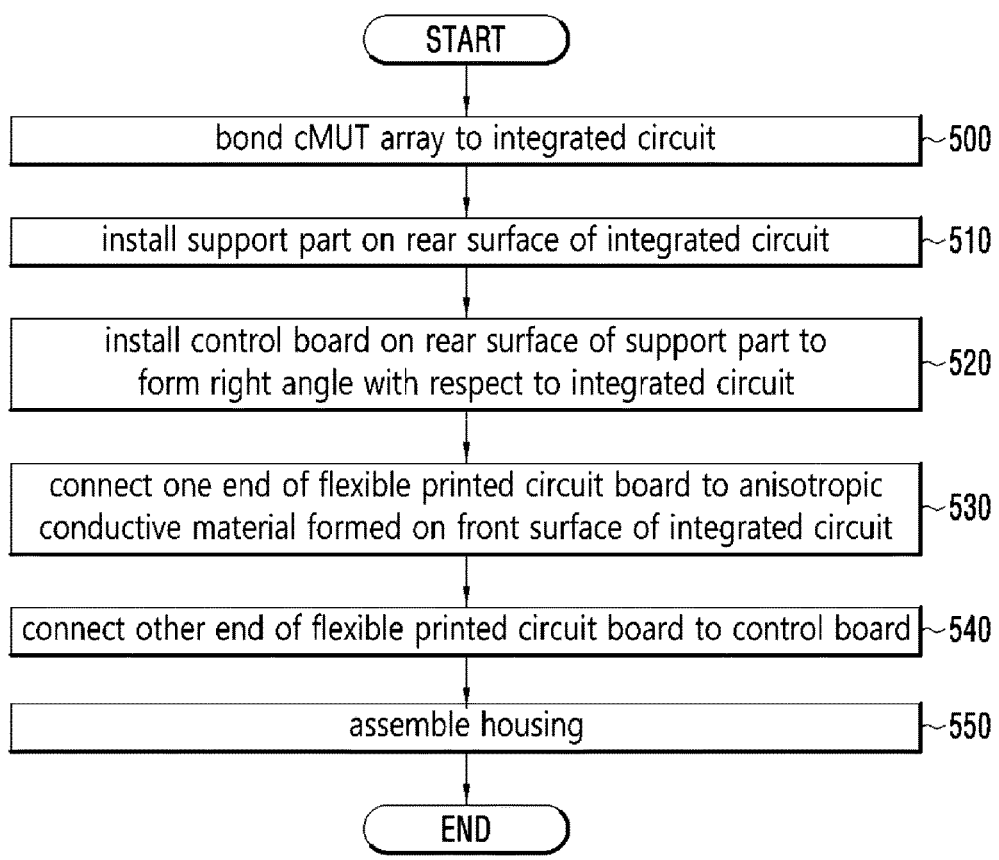

ULTRASONIC PROBE AND MANUFACTURING METHOD THEREOF

CROSS-REFERENCE TO RELATED APPLICATION

This application claims the benefit of Korean Patent Application No. 10-2014-0048771, filed on Apr. 23, 2014 in the Korean Intellectual Property Office, the disclosure of which is incorporated herein by reference.

BACKGROUND

1. Field

Exemplary embodiments of the present disclosure relate to an ultrasonic probe.

2. Description of the Related Art

An ultrasonic imaging apparatus operates to irradiate ultrasonic waves through the surface of an object toward a target portion within the object, and receive an ultrasonic echo signal reflected from the target portion to obtain a cross-sectional image of a soft tissue or bloodstream in a non-invasive manner.

The ultrasonic imaging apparatuses are smaller in size and cheaper compared to other image diagnostic devices (e.g., X-ray diagnostic device, computerized tomography (CT) scanner, magnetic resonance imaging (MRI), nuclear medicine diagnostic device, etc.). In addition, the ultrasonic imaging apparatus may enable real-time display of a diagnosis image and is very safe because there is no risk of X-ray exposure. Thus, ultrasonic imaging apparatuses are widely used in diagnosis procedures in the fields of obstetrics and gynecology, diagnosis procedures for the heart and abdomen, and urology diagnosis.

An ultrasonic imaging apparatus includes an ultrasonic probe to transmit ultrasonic waves to an object and receive ultrasonic echo waves reflected from the object to obtain an internal image of the subject.

SUMMARY

Therefore, it is an aspect of the exemplary embodiments to provide an ultrasonic probe having an integrated circuit, to which a cMUT array is bonded, connected to a control board by a flexible printed circuit board.

Additional aspects of the disclosure will be set forth in part in the description which follows and, in part, will be obvious from the description, or may be learned by practice of the disclosure.

In accordance with an aspect of an exemplary embodiment, there is provided an ultrasonic probe including a capacitive micromachined ultrasonic transducer (cMUT) array configured to generate ultrasonic waves, an integrated circuit to which the cMUT array is bonded, and a flexible printed circuit board having one end connected to the integrated circuit to output signals to the integrated circuit, wherein the integrated circuit includes pads provided on the integrated circuit and an anisotropic conductive film (ACF) provided on the pads, and the one end of the flexible printed circuit board is connected to the ACF to thereby connect the flexible printed circuit board to the integrated circuit In accordance with another aspect of an exemplary embodiment, there is provided an ultrasonic probe including an integrated circuit, a capacitive micromachined ultrasonic transducer (CMUT) array bonded to a region of the integrated circuit, pads provided on a region of the integrated circuit except for the region to which the cMUT array is bonded, an anisotropic conductive film (ACF) provided on the pads, and a flexible printed circuit board having one end thereof connected to the ACF to output a signal to the integrated circuit.

In accordance with another aspect of an exemplary embodiment, there is provided a method of manufacturing an ultrasonic probe including: bonding a capacitive micromachined ultrasonic transducer (cMUT) array configured to generate ultrasonic waves to an integrated circuit including pads; providing an anisotropic conductive film (ACF) on the pads of the integrated circuit; and connecting one end of a flexible printed circuit board to the ACF by applying at least one of heat and pressure to the ACF.

BRIEF DESCRIPTION OF THE DRAWINGS

These and/or other aspects of the exemplary embodiments will become apparent and more readily appreciated from the following description of the exemplary embodiments, taken in conjunction with the accompanying drawings of which:

FIG. 10 is a flowchart showing a method of manufacturing an ultrasonic probe in accordance with an exemplary embodiment.

DETAILED DESCRIPTION

Figure 1:
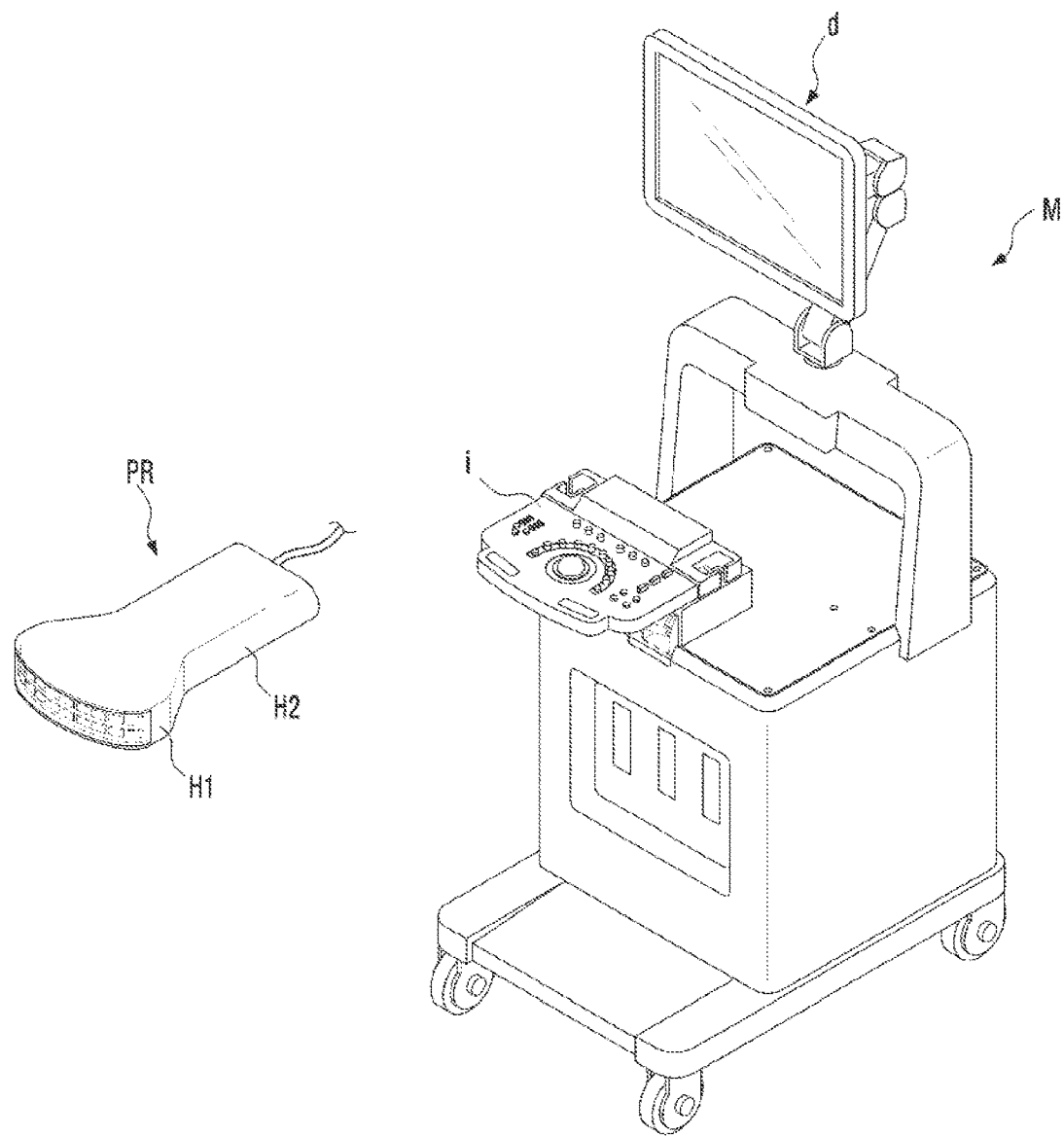
FIG. 1 is a perspective view illustrating an ultrasonic imaging apparatus in accordance with an exemplary embodiment.

Reference will now be made in detail to the exemplary embodiments, examples of which are illustrated in the accompanying drawings, wherein like reference numerals refer to like elements throughout.

Figure 2:
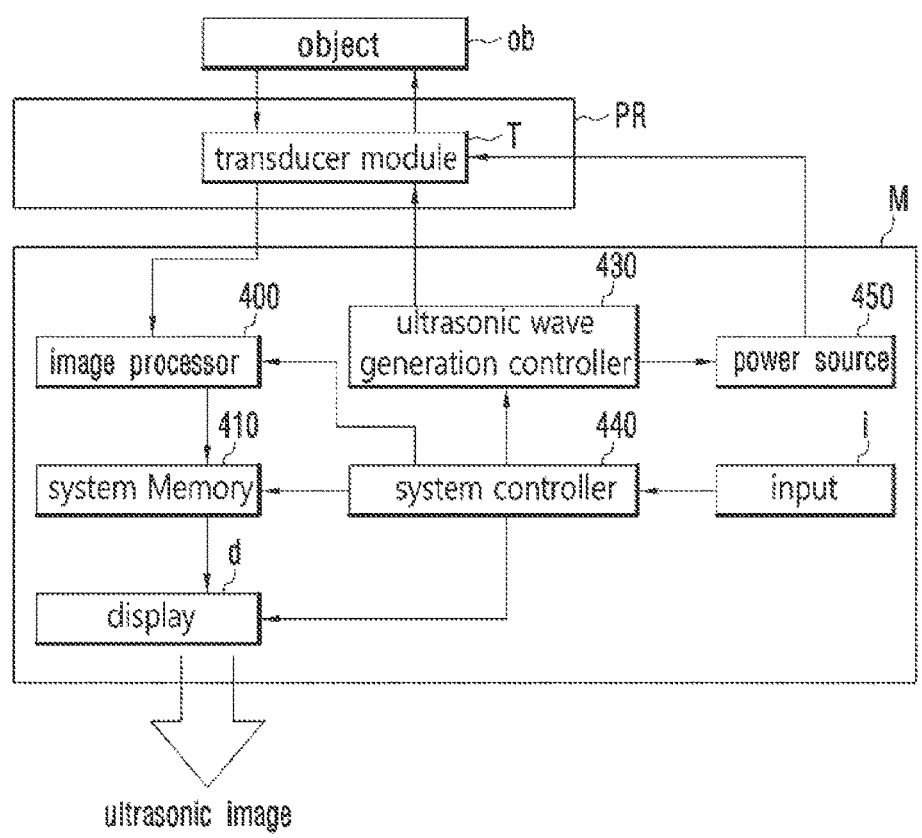
FIG. 2 is a block diagram illustrating an ultrasonic imaging apparatus in accordance with an exemplary embodiment.

FIG. 1 is a perspective view illustrating an ultrasonic imaging apparatus in accordance with an exemplary embodiment, and FIG. 2 is a block diagram illustrating an ultrasonic imaging apparatus in accordance with an exemplary embodiment.

Referring to FIGS. 1 and 2, the ultrasonic imaging apparatus includes an ultrasonic probe PR configured to radiate ultrasonic waves to an object ob, receive echo ultrasonic waves from the object ob and convert the received echo ultrasonic waves into electric signals (hereinafter, referred to as ultrasonic signals), and a main body M configured to generate an ultrasonic image based on the ultrasonic signals. As shown in FIG. 1, the main body M may be provided using a workstation connected to the ultrasonic probe PR, and including an input i and a display d.

As shown in FIG. 2, the main body M includes an image processor 400 configured to generate an image based on an ultrasonic signal output from the ultrasonic probe PR, a system memory 410 configured to store the ultrasonic image generated by the image processor 400, a display d configured to display the ultrasonic image generated by the image processor 400 or the ultrasonic image stored in the system memory 410, an ultrasonic wave generation controller 430 configured to control ultrasonic radiation of a transducer module T, a power source 450 configured to apply a predetermined alternating current to the transducer module T, an input i configured to receive a predetermined instruction or command from a user to control the ultrasonic imaging apparatus, and a system controller 440 configured to control the overall operation of the ultrasonic imaging apparatus by controlling the ultrasonic wave generation controller 430, the image processor 400, the system memory 410 and the display d.

The image processor 400 generates an image that enables a person (e.g., a surgeon or a patient) to visually check the inside of an object ob, that is, a human body, based on the ultrasonic signal.

The image processor 400 transmits an ultrasonic image generated by use of an ultrasonic signal to the system memory 410 or the display d.

In addition, the image processor 400 may further perform an additional image processing operation on the ultrasonic image according to an exemplary embodiment. For example, the image processor 400 may further perform a post-processing operation, such as correcting or readjusting a contrast, brightness or sharpness of an ultrasonic image.

In addition, a certain portion of an ultrasonic image may be represented with a different color or indicated with a marker by use of a generally known technology so as to be distinguished from other portions of the ultrasonic image and spotlighted on the display d. In addition, a plurality of ultrasonic images may be generated to generate a three dimensional ultrasonic image using the plurality of ultrasonic images. The image processor 400 may perform such an additional image processing operation according a predetermined setting, or according to an instruction or command that is input by a user through the input i.

The system memory 410 stores an ultrasonic image generated from the image processor 400 or an ultrasonic image having been subjected to an additional post processing, and the display d displays the ultrasonic image generated from the image processor 400 or stored in the system memory 410, thereby enabling a user to visually check the internal structure or tissues of an object ob.

The ultrasonic wave generation controller 430, according to a command by the system controller 440, generates a transmission pulse and transmits the generated pulse to the transducer module T. The transducer module T generates ultrasonic waves in response to the transmission pulse output from the ultrasonic wave generation controller 430, and radiates the generated ultrasonic waves to the object ob.

In addition, the ultrasonic wave generation controller 430 may generate an additional control signal for the power source 450 such that the power source 450 applies a predetermined alternating current to the transducer module T.

The system controller 440 controls overall operations of the ultrasonic imaging apparatus including the ultrasonic wave generation controller 430, the image processor 400, the system memory 410 and the display d.

According to an exemplary embodiment, the system controller 440 may control an operation of the ultrasonic imaging apparatus according to a predetermined setting, or may generate a control command according to an instruction or a command that is input by a user through the input i, and control the operation of the ultrasonic imaging apparatus.

The input i receives a predetermined instruction or command from a user to control the ultrasonic imaging apparatus. The input i may include a user interface, such as a keyboard, a mouse, a trackball, a touch screen or a paddle.

The ultrasonic probe PR collects information about a target portion of an object ob by use of the ultrasonic waves.

Referring to FIG. 2, the ultrasonic probe PR includes the transducer module T configured to generate ultrasonic waves, radiate the generated ultrasonic waves to a target portion inside the object ob, and receive echo ultrasonic waves.

The transducer module T generates ultrasonic waves according to a pulse signal or an alternating current signal that is applied to the transducer module T, and radiates the generated ultrasonic waves to the object ob. The ultrasonic waves radiated to the object ob are reflected from a target portion inside the object ob. The transducer module T receives the reflected echo ultrasonic waves, and converts the echo ultrasonic waves into electric signals, thereby generating ultrasonic signals.

The transducer module T receives power from a power supply device outside the transducer module T or a charge storage device inside the transducer module T, for example, a battery. When power is supplied, a piezoelectric vibrator or a thin film forming the transducer module T vibrates. The transducer module T radiates ultrasonic waves, which are generated by vibration of the piezoelectric vibrator or thin film, to the object. Upon reception of echo ultrasonic waves reflected by the object, the piezoelectric vibrator or thin film forming the transducer module T vibrates in response the received echo ultrasonic waves. The transducer module T generates alternating current of a frequency corresponding to a vibration frequency of the piezoelectric vibration or the thin film, thereby converting the ultrasonic waves into electric signals (hereinafter, referred to as ultrasonic signals).

Figure 3:
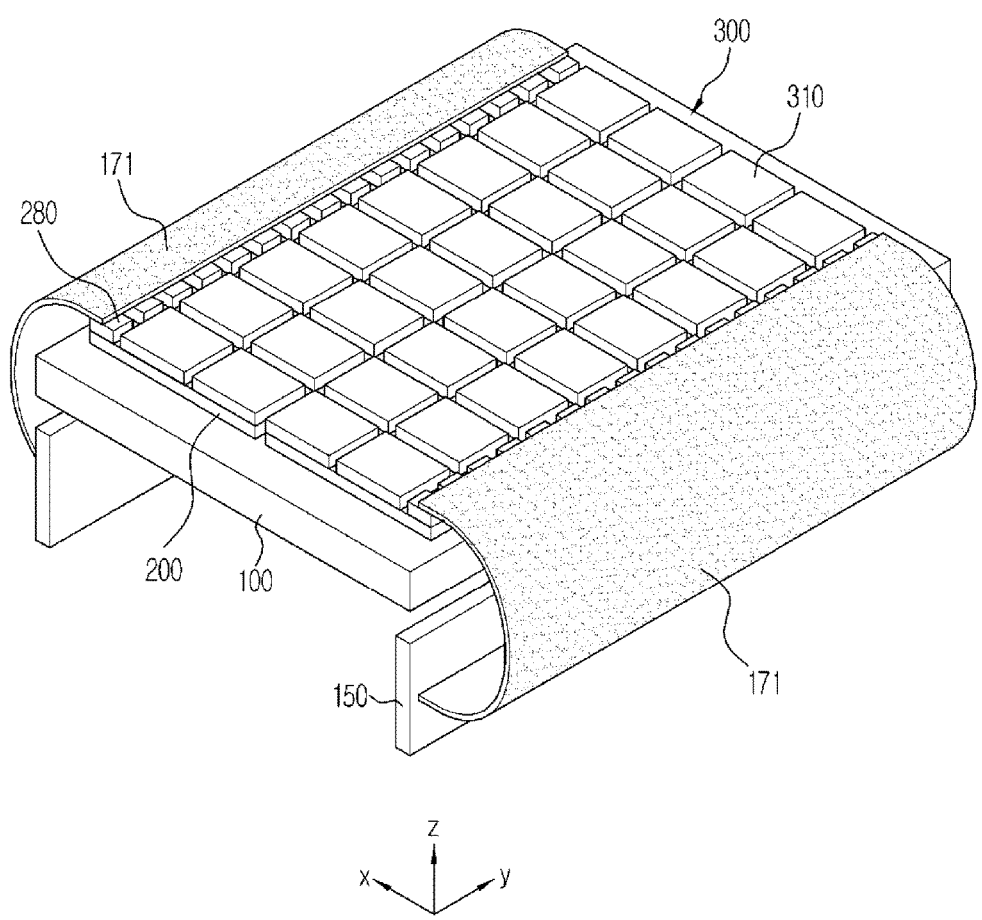
FIG. 3 is a perspective view illustrating a transducer module of an ultrasonic probe in accordance with an exemplary embodiment.
Figure 4:
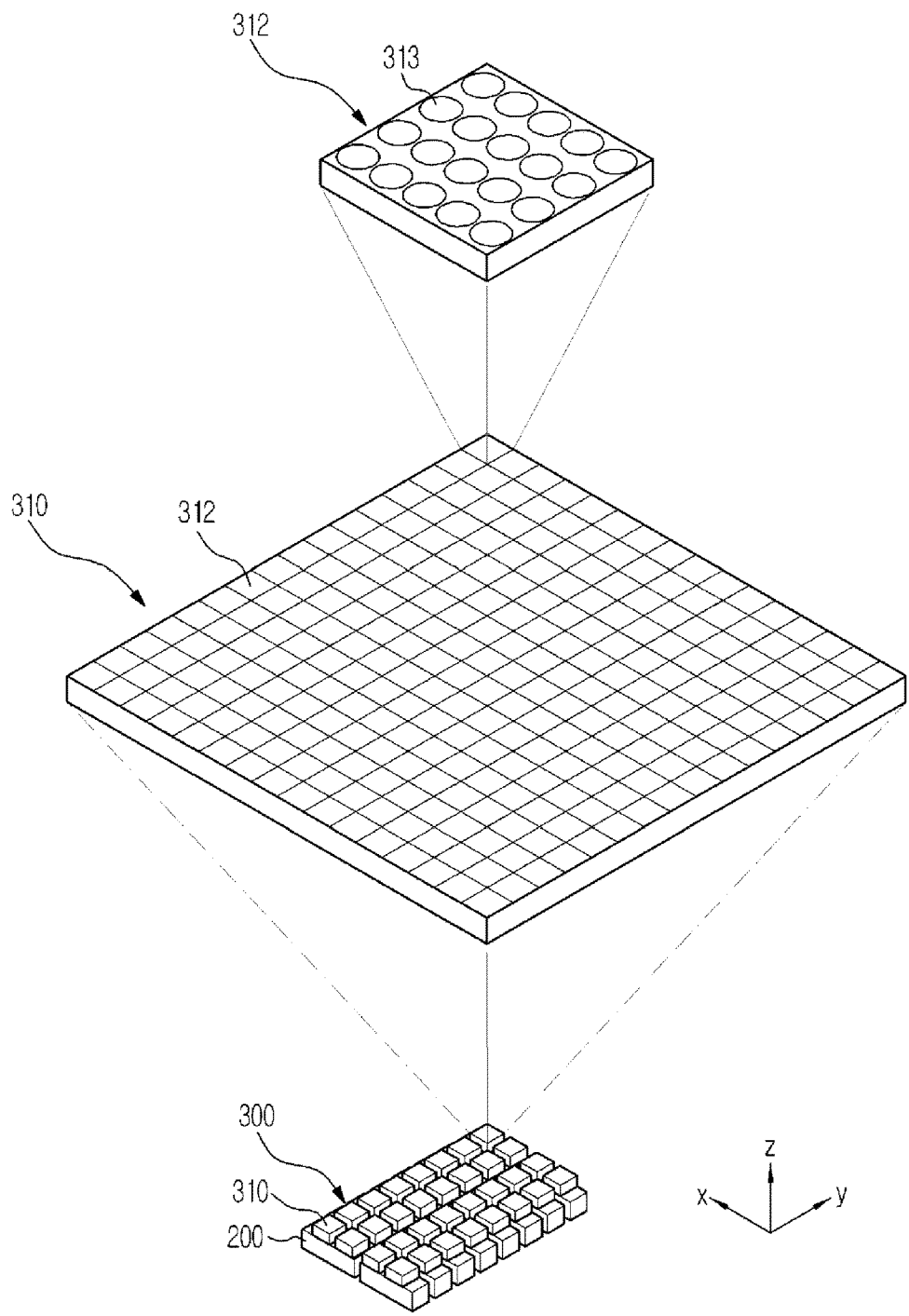
FIG. 4 is a conceptual view illustrating a configuration of a transducer array of a transducer module of FIG. 3.
Figure 5:
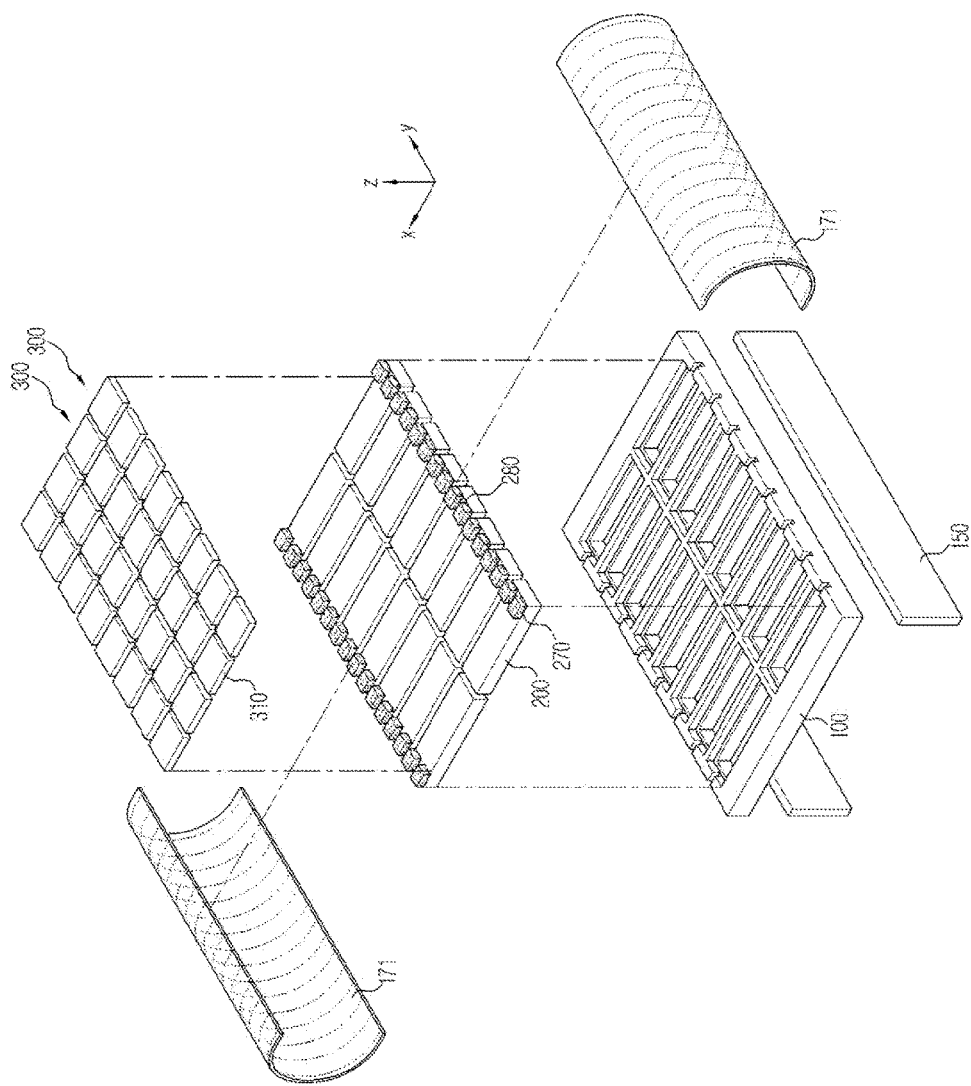
FIG. 5 is an exploded perspective view illustrating a configuration of a transducer module of an ultrasonic probe in accordance with an exemplary embodiment.
Figure 6:
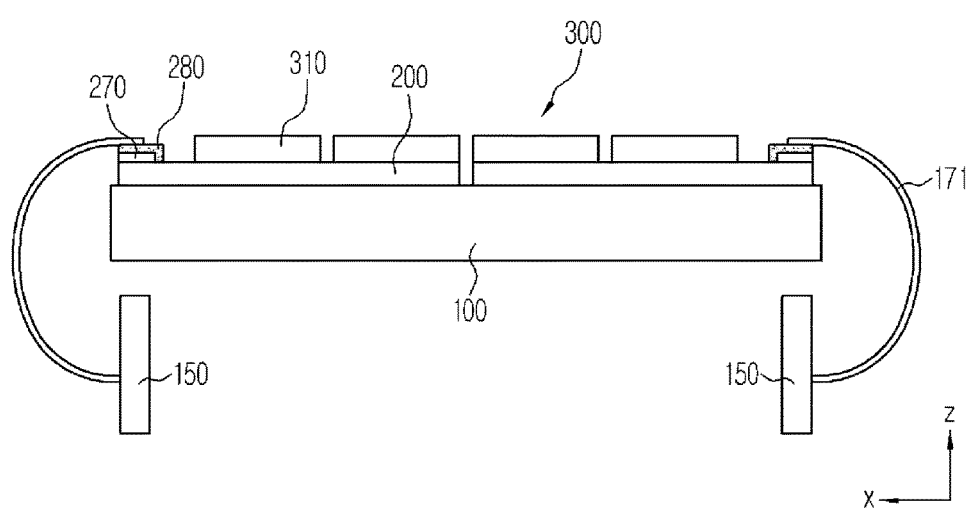
FIG. 6 is a cross sectional view illustrating a configuration of a transducer module of an ultrasonic probe in accordance with an exemplary embodiment.

Hereinafter, the transducer module T will be described with reference to FIGS. 3 to 6 in detail. FIG. 3 is a perspective view illustrating a transducer module of an ultrasonic probe in accordance with an exemplary embodiment, FIG. 4 is a conceptual view illustrating a configuration of a transducer array of a transducer module of FIG. 3, FIG. 5 is an exploded perspective view illustrating a configuration of a transducer module of an ultrasonic probe in accordance with an exemplary embodiment, and FIG. 6 is a cross sectional view illustrating a configuration of a transducer module of an ultrasonic probe in accordance with an exemplary embodiment.

Referring to FIG. 3, the transducer module T includes a transducer array 300 to transmit and receive ultrasonic waves, an integrated circuit 200 to which the transducer array 300 is bonded, a control board 150 to output a transmission signal for generating ultrasonic waves to the integrated circuit 200, a flexible printed circuit board 171 connecting the integrated circuit 200 to the control board 150 to output the transmission signal output from the control board 150 to the integrated circuit 200, and a support part 100 configured to support the integrated circuit 200.

The transducer array 300 includes a plurality of transducer elements 312 to transmit ultrasonic waves. The transducer element 312 may be provided using a magnetostrictive ultrasonic transducer using a magnetostrictive effect, which is primarily used in a conventional ultrasonic probe device, a piezoelectric ultrasonic transducer or a piezoelectric micromachined ultrasonic transducer using a piezoelectric effect of a piezoelectric material, or a capacitive micromachined ultrasonic transducer (hereinafter, referred to as cMUT), which transmits and receives ultrasonic waves using vibration of several hundreds or thousands of micromachined thin films. The following description describes an example using the cMUT as the transducer element 312.

The cMUT array 300 may be provided in a two dimensional array as shown in FIGS. 3 to 6.

A tile 310 is a basic unit forming the cMUT array 300. The tile 310 is formed of the transducer elements 312 arranged in a two dimensional array. The transducer element 312 includes a plurality of thin films 313 that are arranged in a two dimensional array and vibrate upon reception of an electric signal.

For example, as shown in FIG. 4, the cMUT array 300 is provided in a two dimensional array of a 4×8 size formed of 32 tiles 310. A single tile 310 is provided in a two dimensional array of a 16×16 size formed of 256 transducer elements 312. A single transducer element 312 may include 20 to 25 thin films 313 that generate ultrasonic waves while vibrating upon reception of electric signals. In this case, the cMUT array 300 may include a total of 163,840 to 204,800 thin films 313.

As described above, when the cMUT array 300, that is, a transducer of the ultrasonic probe PR, has a two dimensional array of a 4×8 size formed of 32 tiles 310, each column of the cMUT array 300 is bonded to two integrated circuits 200 that may independently apply electric signals to upper two tiles 310 and lower two tiles 310 of each column.

For example, the cMUT array 300 is bonded to the integrated circuit 200, which may be an Application Specific Integrated Circuits (ASIC), by a flip chip bonding method. The integrated circuit 200 having the cMUT array 300 bonded thereto may be connected to the control board 150 through the flexible printed circuit board 171. This feature will be described later in detail. When a transmission signal is applied through the control board 150, the integrated circuit 200 controls the transmission signal applied to the cMUT array 30 according to logic, thereby adjusting generation of ultrasonic waves. The transmission signal applied from the control board 150 may be a transmission pulse output from the ultrasonic wave generation controller 430 of the main body M. According to another exemplary embodiment, the control board 150 may directly generate transmission pulses and output the generated transmission pulses to the integrated circuit 200 through the flexible printed circuit board 171.

In order to support the tile structure of the cMUT array 300, the support part 100 may be provided in the form of a frame having a groove corresponding to the shape of the tile of the cMUT array 300. Referring to FIG. 5, the support part 100 may have a groove structure to mount each integrated circuit 200 having the tile 310 bonded thereto.

As shown in FIGS. 3, 5 and 6, the flexible printed circuit board 171 is attached to the integrated circuit 200 to which the cMUT array 300 is bonded.

Referring to FIGS. 3 and 5, the integrated circuit 200 is provided at both end portions along a y axis direction with pads 270 connected to the flexible printed circuit board 171. Electrodes P of the flexible printed circuit board 171 are connected to the pads 270 of the integrated circuit 200. The flexible printed circuit board 171 delivers the transmission signal output from the control board 150 to the integrated circuit 200.

The flexible printed circuit board 171 may be directly connected to the pad 270. However, according to the present exemplary embodiment, an anisotropic conductive film ACF 280 is attached to an upper portion of the pad 270 and the flexible printed circuit board 171 is attached to an upper portion of the ACF 280.

Figure 7:
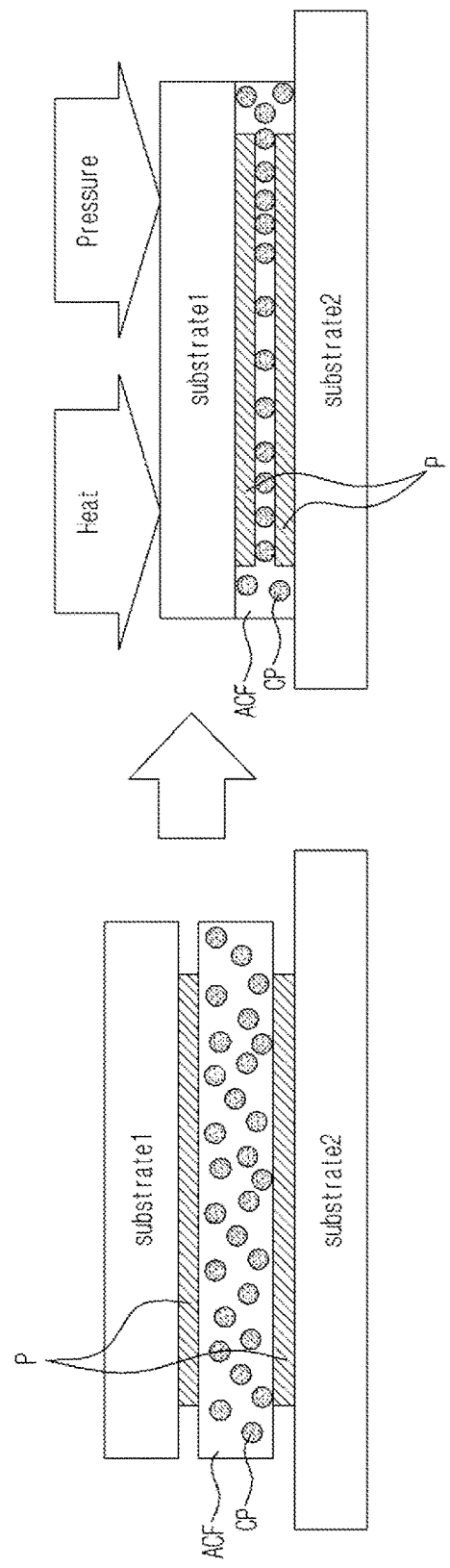
FIG. 7 is a conceptual view illustrating a bonding process using an anisotropic conductive film (ACF)
Figure 8:
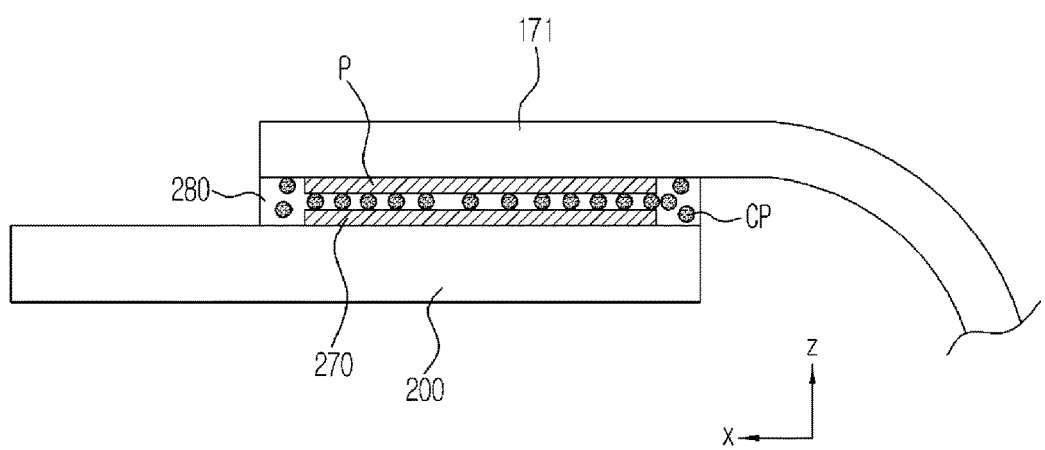
FIG. 8 is a conceptual view illustrating a bonding process of an integrated circuit and a flexible printed circuit board using an ACF.

FIG. 7 is a conceptual view illustrating a bonding process using an anisotropic conductive film (ACF), and FIG. 8 is a conceptual view illustrating a bonding process of an integrated circuit and a flexible printed circuit board using an ACF.

The ACF 280 is provided as conductive particles dispersed in thermosetting epoxy or acryl resin in the form of a film. The ACF 280 allows various electronic parts to be mechanically or electrically bonded through heat and pressure application.

Referring to FIG. 7, the ACF is provided between electrodes P of substrate 1 and substrate 2 configured to be bonded to each other. As heat and pressure are applied to substrate 1, substrate 1 and substrate 2 are mechanically bonded to each other by the ACF, and electrically bonded to each other by the conductive particles CP inside the ACF.

Referring to FIG. 8, in a state in which the ACF 280 is disposed between the pad 270 of the integrated circuit 200 and the electrode P of the flexible printed circuit board 171, when heat and pressure are applied to the flexible printed circuit board 171 or the integrated circuit 200, the ACF 280 obtains fluidity. In addition, the conductive particles CP between the pad 270 and the electrode P make physical contact with the pad 270 and the electrode P, thereby conducting the pad 270 with the electrode P.

As the ACF 280 is cured, the flexible printed circuit board 171 is mechanically attached to the integrated circuit 200. The conductive particles CP of the ACF 280 electrically connect the pad 270 of the integrated circuit 200 to the electrode P of the flexible printed circuit board 171. The signal output from the flexible printed circuit board 171 is transmitted to the integrated circuit 200 by the conductive particles CP.

As shown in FIGS. 3, 5 and 6, the flexible printed circuit boards 171 may be bonded to both end portions of the integrated circuit 200 by the ACF 280. Alternatively, a single flexible printed circuit board 171 may be bonded to one end portion of the integrated circuit 200 by the ACF 280.

The other end of the flexible printed circuit board 171 bonded to the integrated circuit 200 is connected to the control board 150. The control board 150 may be implemented using a printed circuit board on which electronic devices are mounted to generate transmission signals and process ultrasonic signals.

The other end of the flexible printed circuit board 171 may be connected to the control board 150 through various types of connectors, and may be connected to electrodes of the control board 150 by the ACF 280 in the same manner as the above.

Referring to FIGS. 3, 5 and 6, the two control boards 150 may be provided at a rear side of the support part 100 while being perpendicular to the support part 100 and the integrated circuit 200. Although the control board 150 is illustrated as being perpendicular to the support part 100 and the integrated circuit 200, the disposition of the control board 150 is not limited to being perpendicular to the support part 100 and the integrated circuit 200, as long as the control board 150 is not stacked in parallel to the support part 100 and the integrated circuit 200 at a rear side of the support part 100. That is, the control board 150 may be slantingly installed with respect to a rear surface of the support part 100 while forming a predetermined angle.

The control board 150 is installed to be perpendicular to the rear surface of the support part 100, and the flexible printed circuit board 171 is bonded to the electrodes of the control board 150, thereby preventing a surface at which the ultrasonic probe PR makes contact with a human body, hereinafter, also referred to as a footprint, from being increased to be larger than an area of the integrated circuit 200.

Figure 9:
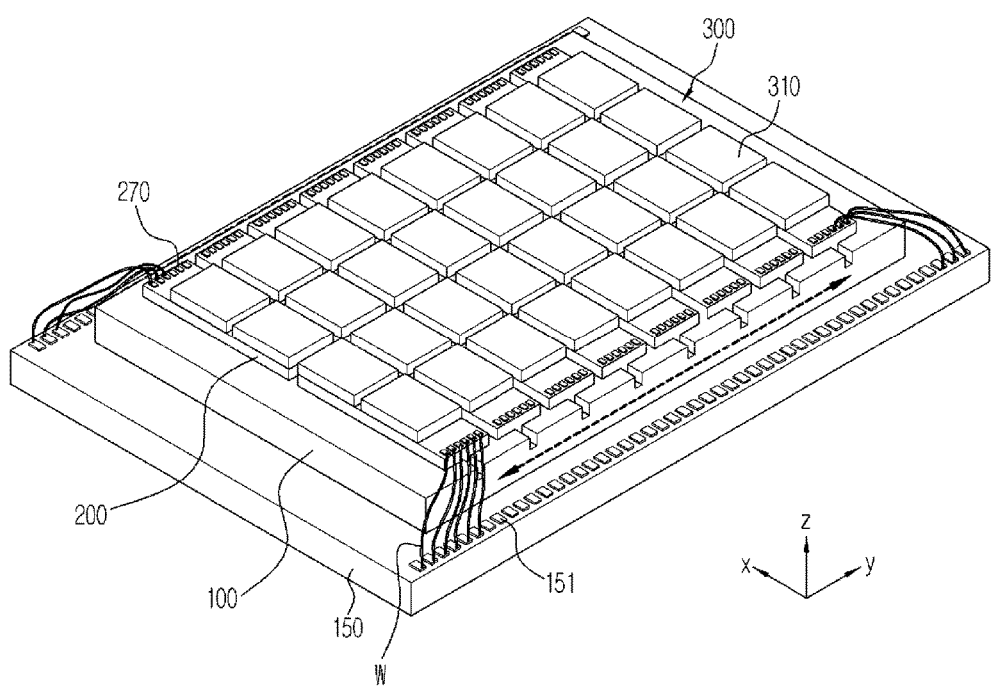
FIG. 9 is a perspective view illustrating a transducer module in a stacked structure having a control board connected to an integrated circuit through a wire.

FIG. 9 is a perspective view illustrating a transducer module of a stacked structure having a control board connected to an integrated circuit through a wire.

Referring to FIG. 9, the control board 150 is installed on a rear surface of the integrated circuit 200 in parallel to the integrated circuit 200, forming a stacking structure. The integrated circuit 200 is connected to the control board 150 by a wire W. In this case, the control board 150 is provided to have an area larger than that of the integrated circuit 200 in order to connect the pad 270 of the integrated circuit 200 to the control board 150 by a wire W as shown in FIG. 9.

When the transducer module T is manufactured as shown in FIG. 9, the integrated circuit 200 has an x-axis direction length of about 2.6 cm, but the control board 150 has an x-axis direction length of about 5 cm, which is a length twice the x-axis direction length of the integrated circuit 200. In this case, the x-axis direction of the ultrasonic probe PR is increased by 3 cm to 5 cm or above, which degrades the transmission and reception efficiency of the ultrasonic waves.

In addition, when the integrated circuit 200 is connected to the control board 150 by a wiring, the area of the control board 150 needs to be provided to be larger than the integrated circuit 200 to prevent wires W from being interfered with and to lower the process complexity, which ends up increasing the above described shortcomings associated with the transmission and reception efficiency of the ultrasonic waves.

According to an exemplary embodiment, the integrated circuit 200 is not connected to the control board 150 by a wire W, but is connected by the flexible printed circuit board 171, thereby preventing the process complexity arising from the wiring. In addition, according to an exemplary embodiment, the control board 150 is installed to be perpendicular to the support part 100 and the integrated circuit 200 at a rear side of the support part 100, thereby preventing the footprint of the ultrasonic probe PR from being increased.

In addition, if the control board 150 is formed to be perpendicular to the support part 100 and the integrated circuit 200 at a rear surface of the support part 100, the control board 150 may be provided inside a rear portion H2 of a housing whose inside is relatively marginal, that is, inside a portion of the housing which is gripped by a user. Accordingly, the inside space of the ultrasonic probe PR is more efficiently used. If the control board 150 is installed in a stacked structure as shown in FIG. 9, the control board 150, as well as the cMUT array 300, the integrated circuit 200 and the support part 100, need to be positioned inside a front portion H1 of the housing. In this case, the inside space of the front portion H1 of the housing needs to be increased. Accordingly, the footprint of the ultrasonic probe PR may be further increased.

Accordingly, when the control board 150 is installed according to the configuration in FIG. 6, the footprint of the ultrasonic probe PR is reduced, and the inside space of the ultrasonic probe PR is efficiently used, and thus, the freedom of design of the ultrasonic probe PR is improved.

FIG. 10 is a flowchart showing a method of manufacturing an ultrasonic probe in accordance with an exemplary embodiment.

Referring to FIG. 10, the cMUT array 300 is bonded to the integrated circuit 200 at operation 500, and the support part 100 is installed on the rear surface of the integrated circuit 200 at operation 510.

The cMUT array 300 may be bonded to the integrated circuit 200, such as an ASIC (Application Specific Integrated Circuits), using a flip chip bonding technique. As described above, when the cMUT array 300, that is, a transducer of the ultrasonic probe PR, has a two dimensional array of a 4×8 size formed of 32 tiles 310, each column of the cMUT array 300 is bonded to two integrated circuits 200 that each control electric signals applied to two upper tiles 310 and two lower tiles 310 of each column.

In order to support the tile structure of the cMUT array 300, the support part 100 may be provided in the form of a frame having a groove corresponding to the shape of the tile of the cMUT array 300. Referring to FIG. 5, the support part 100 may have a groove structure in which each integrated circuit 200 having the tile 310 forming the cMUT array 300 is mounted.

The control board 150 is installed at the rear surface of the support part 100 to form a right angle with the integrated circuit 200 and the support part 100 at operation 520. The flexible printed circuit board 171 has one end thereof connected to anisotropic conductive material formed on a front surface of the integrated circuit 200 at operation 530, and the other end thereof connected to the control board 150 at operation 540. The control board 150 may be installed first, and then the flexible printed circuit board 171 may be installed. Alternatively, the flexible printed circuit board 171 may be bonded to the integrated circuit 200 first, and then the control 150 board may be installed. That is, the manufacturing order is not limited to any particular order.

As shown in FIGS. 3, 5 and 6, the flexible printed circuit board 171 is attached to the integrated circuit 200 to which the cMUT array 300 is bonded. The integrated circuit 200 is provided at both end portions in a y axis direction with the pads 270 connected to the flexible printed circuit board 171. The electrodes P of the flexible printed circuit board 171 are connected to the pads 270 of the integrated circuit 200. The flexible printed circuit board 171 delivers the transmission signal output from the control board 150 to the integrated circuit 200.

The flexible printed circuit board 171 may be directly connected to the pad 270. However, according to the present exemplary embodiment, the anisotropic conductive film ACF 280 is attached to an upper portion of the pad 270 and the flexible printed circuit board 171 is attached to an upper portion of the ACF 280.

The ACF 280 is provided as conductive particles dispersed in thermosetting epoxy or acryl resin in the form of a film. The ACF 280 allows various electronic parts to be mechanically or electrically bonded through heat and pressure application processes.

Referring to FIG. 8, in a state in which the ACF 280 is disposed between the pad 270 of the integrated circuit 200 and the electrode P of the flexible printed circuit board 171, when heat and pressure are applied to the flexible printed circuit board 171 or the integrated circuit 200, the ACF 280 obtains fluidity. In addition, the conductive particles CP between the pad 270 and the electrode P make physical contact with the pad 270 and the electrode P, thereby conducting the pad 270 with the electrode P.

As the ACF 280 is cured, the flexible printed circuit board 171 is mechanically attached to the integrated circuit 200. The conductive particles CP of the ACF 280 electrically connect the pad 270 of the integrated circuit 200 to the electrode P of the flexible printed circuit board 171. The signal output from the flexible printed circuit board 171 is transmitted to the integrated circuit 200 by the conductive particles CP.

The other end of the flexible printed circuit board 171 bonded to the integrated circuit 200 is connected to the control board 150. The control board 150 may be implemented using a printed circuit board on which electronic devices configured to generate transmission signals and process ultrasonic signals are mounted.

The other end of the flexible printed circuit board 171 may be connected to the control board 150 through various types of connectors, or may be connected to electrodes of the control board 150 by the ACF 280 in the same manner as described above.

Although the two control boards 150 are illustrated as being provided at a rear side of the support part 100 while being perpendicular to the support part 100 and the integrated circuit 200 in FIGS. 3, 5 and 6, the disposition of the control board 150 is not limited to this configuration, as long as the control board 150 is provided at a rear side of the support part 100 in a stacked structure and is not parallel to the support part 100 and the integrated circuit 200. That is, the control board 150 may be slantingly installed with respect to a rear surface of the support part 100 while forming a predetermined angle.

As the control board 150 is installed to be perpendicular to the support part 100 and the flexible printed circuit board 171 at a rear side of the support 100 part, and the flexible printed circuit board 171 is bonded to the electrodes of the control board 150, the footprint of the ultrasonic probe PR is prevented from being increased to be larger than the area of the integrated circuit 200.

Once the control board 150 and the flexible printed circuit board 171 are installed, a housing is assembled, and thus the ultrasonic probe PR is manufactured at operation 550. When the control board 150 is formed to be perpendicular to the support part 100 at a rear surface of the support part 100, the control part 150 may be provided inside the rear portion H2 of the housing whose inside has a marginal space, that is, a portion of the housing which is gripped by a user. Accordingly, the inside space of the ultrasonic probe PR is more efficiently used.

As is apparent from the above description, the area at which the ultrasonic probe makes contact with a human body is reduced without having to reduce a size of the cMUT array.

In addition, the integrated circuit is connected to the control board by use of a flexible printed circuit board without using wiring, so that the manufacturing and processing operations are reduced in complexity.

Although a few exemplary embodiments have been shown and described, it would be appreciated by those skilled in the art that changes may be made in these exemplary embodiments without departing from the principles and spirit of the exemplary embodiments, the scope of which is defined in the claims and their equivalents.

What is claimed is:

1. An ultrasonic probe comprising:
   a capacitive micromachined ultrasonic transducer (cMUT) array configured to generate ultrasonic waves;
   an integrated circuit comprising:
      a first surface bonded to the cMUT array,
      pads configured to be interfaced with the cMUT array and aligned in a row on the first surface,
      an anisotropic conductive film (ACF) provided on the pads, and
      a second surface disposed opposite to the first surface;
   a support part provided on the second surface of the integrated circuit, to support the integrated circuit;
   a control board which is configured to control the integrated circuit and comprises:
      an edge portion which is disposed underneath a lower surface of the support part and extends along the row of the pads, and
      a side surface which is connected to the edge portion and is perpendicular to the lower surface of the support part, wherein the side surface of the control hoard is extended in a direction away from the support part in an alignment with an edge of the lower surface of the support part, so that the control board is provided within a footprint of the lower surface of the support part; and
   a flexible printed circuit board comprising:
      a first end placed on the pads and electrically connected to the pads through the ACF, to output signals to the integrated circuit,
      a body extending from the ACF along a portion of the side surface of the control board, and
      a second end connected to a connector disposed on the side surface,
   wherein the cMUT array comprises a plurality of tiles bonded to the integrated circuit and spaced apart from each other and the pads.

2. The ultrasonic probe of claim 1, wherein the control board is configured to output signals to the integrated circuit through the flexible printed circuit board.

3. The ultrasonic probe of claim 1, wherein the ACF is configured to bond the flexible printed circuit board to the pads via the ACF in response to heat and pressure being applied to the ACF.

4. The ultrasonic probe of claim 1, wherein the integrated circuit further comprises:
   a first region bonded to the cMUT array; and
   a second region at an outer boundary of the first region, wherein the pads are provided at the second region in the row extending in parallel to ends of the plurality of tiles.

5. The ultrasonic probe of claim 1, further comprising a housing having a front end portion configured to accommodate the cMUT array, the integrated circuit and the flexible printed circuit board therein, and a rear end portion configured to be gripped by a user.

6. The ultrasonic probe of claim 5, wherein the control board is installed at a side of the integrated circuit inside the rear end portion of the housing.

7. The ultrasonic probe of claim 1, wherein the second end of the flexible printed circuit board is connected to the connector perpendicularly to the side surface of the control board.

* * * * *